(12) United States Patent
Rodriguez-Kabana et al.

(10) Patent No.: US 6,465,527 B1
(45) Date of Patent: Oct. 15, 2002

(54) IODINATED HYDROCARBON PESTICIDE

(75) Inventors: Rodrigo Rodriguez-Kabana; Arthur G. Appel, both of Auburn, AL (US)

(73) Assignee: Auburn University, Auburn, AL (US)

( * ) Notice: Subject to any disclaimer, the term of this patent is extended or adjusted under 35 U.S.C. 154(b) by 0 days.

(21) Appl. No.: 09/662,262

(22) Filed: Sep. 14, 2000

Related U.S. Application Data (60) Provisional application No. 60/153,814, filed on Sep. 14, 1999.

(51) Int. Cl.⁷ .......................... A01N 29/00; A61K 31/02
(52) U.S. Cl. ........................................ 514/743; 424/405
(58) Field of Search ............................ 514/743; 424/405

(56) References Cited

U.S. PATENT DOCUMENTS 5,444,102 A * 8/1995 Nimitz et al. ................ 521/131

FOREIGN PATENT DOCUMENTS

| JP | 05084873 | * | 4/1993 |
| JP | 10293397 | * | 11/1998 |

* cited by examiner

*Primary Examiner*—Alton Pryor
(74) *Attorney, Agent, or Firm*—Womble Carlyle Sandridge & Rice, PLLC (57) ABSTRACT

Disclosed is both a method and composition for controlling deleterious organisms, such as insects, nematodes and weeds by applying a compound comprised of both mono-iodinated hydrocarbons and di-iodinated hydrocarbons. The combination provides an effective insecticide and nemacide along with herbicidal properties without causing significant harm to the ozone layer. Additionally disclosed is a method of soil fumigation comprising applying to a soil an effective amount of a fumigant selected from diiodinated hydrocarbons, polyiodinated hydrocarbons and their combinations.

26 Claims, 7 Drawing Sheets

IODINATED HYDROCARBON PESTICIDE

This application claims the benefit of U.S. Provisional Application No. 60/153,814 filed September 14, 1999.

FIELD OF INVENTION

The present invention relates generally to the fields of biology and agriculture 10 and more particularly to compositions and methods for use in fumigation of soils and structures.

BACKGROUND

The control of insects, plant pathogens, nematodes and weeds is of central importance to the agriculture industry. In particular, the substantial reduction or elimination of nematode populations in soils is critical to initial plant growth, productivity and life-span. Pathogenic fungi and nematodes develop on the extensive root systems of both annual and perennial crops, severely damaging them. Moreover, they persist in the soil after crop removal and need to be eliminated before replanting of new crops.

Soil fumigation is an essential practice for controlling nematodes and other soil-borne pathogens in many horticultural operations throughout the world. The need for this practice has been increasing due to the production of high-value crops where pathogen susceptible plants are grown in the same field without the benefit of appropriate crop rotations. Fields of this type of production are frequently covered by expensive structures to protect the crops from adverse conditions such as pests and inclement weather. Methyl bromide [MBr], a halogenated hydrocarbon, is the preferred chemical used throughout the world to fumigate soils. This broad-spectrum fumigant is used routinely in a variety of soils and climatic zones because its application requires minimal technology and virtually no knowledge of what pests are present in the soil. It is used extensively for soil fumigation as a commodity quarantine treatment (export and imports) to control a variety of pests on numerous crops and as a structural fumigant for wood destroying pests.

Unfortunately, methyl bromide is an "Ozone-Depleting Substance", i.e., a chemical directly involved in the destruction of the planet's stratospheric ozone layer. Methyl bromide (MBr) is categorized as an ozone-depleting chemical with an ozone-depleting potential (ODP) of greater than 0.2 compared to trichlorofluoromethane (cfc 11), a refrigerant used as a reference gas having an ODP of 1. Evidence on the loss of MBr to the atmosphere after soil fumigation indicates that of the total amount applied to the soil for fumigation, approximately 87% is lost to the atmosphere within seven days. On reaching the stratosphere, MBr undergoes photo-oxidation, releasing bromine atoms which enter the ozone depletion cycle. Thus, its use in agriculture has been scheduled for phase-out. In the United States, methyl bromide will be banned as a soil fumigant in 2005. There is then a need to find alternative chemicals or methods to replace methyl bromide as a soil disinfectant.

Alternative approaches to fumigation include crop rotation, fallowing for at least four years, and use of pathogen and nematode-resistant crops. Unfortunately, resistance to plant pathogens and nematodes is available only in a few crops, and resistant cultivars may not be developed in the foreseeable future for many crops of significant commercial interest. Thus, soil fumigation remains the best alternative for control of plant pathogens and nematodes.

Figure 1:
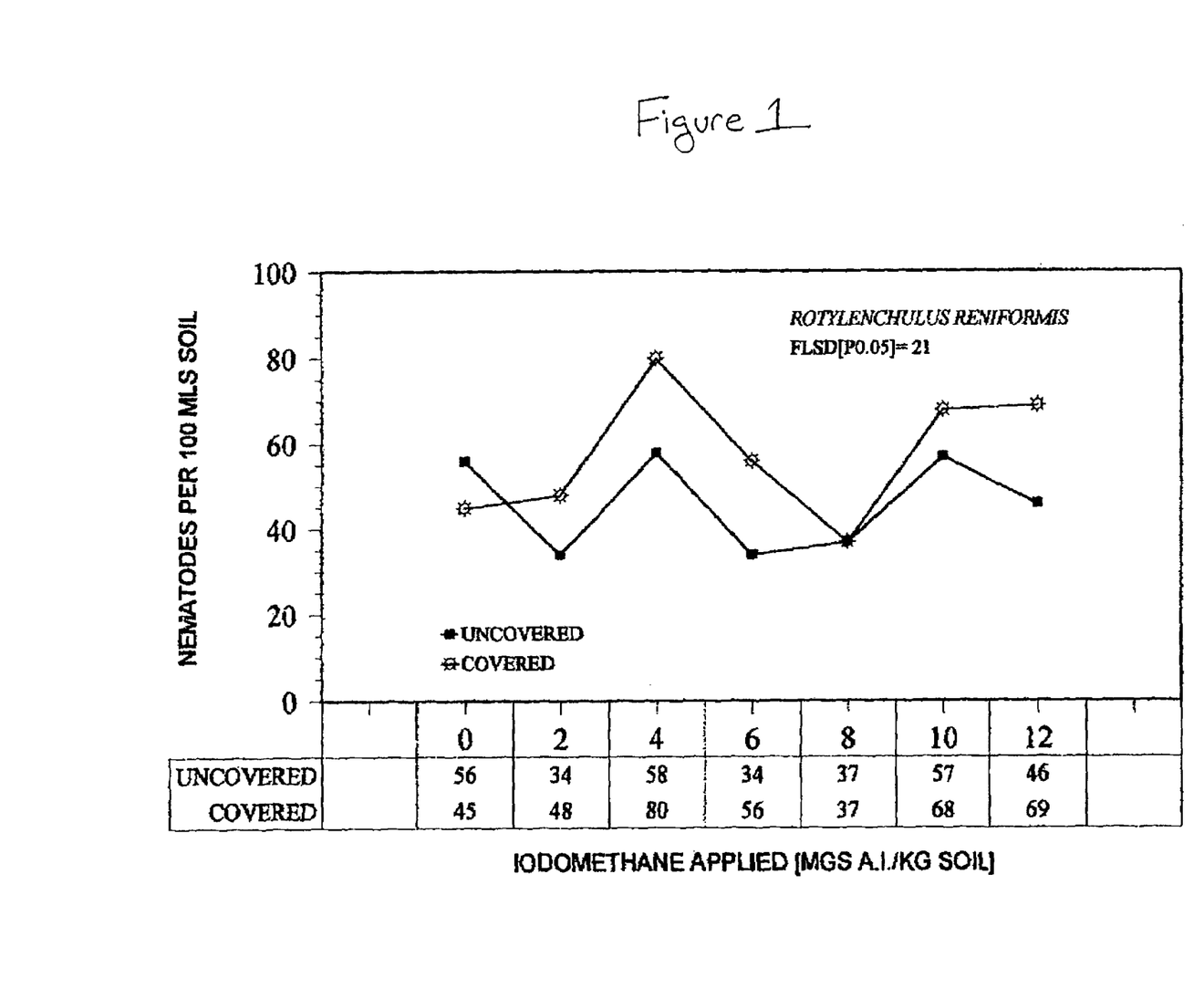
FIG. 1 depicts a graph illustrating the lack of nematicidal qualities of iodomethane when applied to infected soil in various dosages in an uncovered and covered state.

Currently available alternatives to MBr are less effective and more expensive. One proposed substitution for MBr is methyl iodide. Methyl iodide does not have the same deleterious effect on the ozone as MBr, and it acts in a similar fashion as MBr. Unfortunately, methyl iodide requires the same large dosages as MBr and can be relatively ineffective against nematodes. As illustrated in FIG. 1, methyl iodide was tested in a covered and uncovered state in a soil in various quantities up to 12 mg per kg of soil. The graph clearly shows that methyl iodide in such quantities is ineffective against nematodes in either a covered or uncovered environment.

Thus, the loss of MBr would be extremely costly to both agricultural producers and consumers as well as having a substantial impact on the U.S. economy. Nonetheless, it is the general consensus of those working in the field that no approach is currently available that will achieve the same level of broad-spectrum pest management as MBr. Chemical and non-chemical approaches that are available can provide some level of agricultural pest management, but it is generally with narrower activity and lower crop yields and quality. Therefore, there is clearly a need for alternatives to MBr.

SUMMARY

The present invention provides both a method and composition for controlling deleterious organisms, such as insects, nematodes and weeds without causing significant harm to the ozone layer. Such deleterious organisms can be controlled by applying a compound comprised of both monoiodinated hydrocarbons and diiodinated hydrocarbons. Because of the chemical properties of the iodinated hydrocarbons, most notably their solubility, the mono- and diiodinated hydrocarbons can be combined to make an effective insecticidal and nematicidal formulation that gives a similar performance to that of methyl bromide against both insects and nematodes. Additionally, the combination can be an effective herbicide.

Additionally, a method of soil fumigation is provided comprising applying to a soil an effective amount of a fumigant selected from diiodinated hydrocarbons, polyiodinated hydrocarbons and combinations of both.

In one embodiment, the pesticidal composition for controlling deleterious organisms can also contain a compound consisting of mono-iodinated hydrocarbons and di-iodinated hydrocarbons.

Furthermore, a pesticide for controlling deleterious organisms is provided containing a compound selected from the group which consists of diiodinated hydrocarbons, polyiodinated hydrocarbons and combinations thereof

DETAILED DESCRIPTION

The present invention provides both a method and composition for controlling deleterious organisms, such as insects, nematodes and weeds by applying a compound comprised of both mono-iodinated hydrocarbons and diiodinated hydrocarbons. Additionally, a method and composition for soil fumigation is provided comprising diiodinated and polyiodinated hydrocarbons. The compositions and methods provide an effective insecticide and nemacide along with herbicidal properties without causing significant harm to the ozone layer.

Furthermore, the composition and method typically uses about 1/10 the quantity of halogenated hydrocarbon as typically used for methyl bromide and methyl iodide. Typically, over 100 mg per kg of soil is required, wherein the present composition uses about 10 mg to 20 mg per kg of soil depending upon the desired application. Additionally, the present composition can be applied to a soil in a covered or uncovered state. A covered state is usually one where the soil is covered with a plastic sheet to prevent the volatile halogenated hydrocarbons from evaporating from the soil and into the atmosphere.

Monoiodinated hydrocarbons have generally been found to have an increased insecticidal activity over that of diiodinated hydrocarbons in enclosed spaces due, in part, to the increased volatility of the compounds over the diiodinated hydrocarbons. As shown below, Table 1 depicts the toxicity of both monoiodinated and diiodinated hydrocarbons to both the German and the American cockroach after 1 hour of exposure. From the table, it can be seen that the monoiodinated hydrocarbons were more effective in killing both species of cockroaches after only one hour of exposure.

TABLE 1

| | % Mortality after 1 h exposure | |
|---|---|---|
| Compound | German cockroach[1] | American cockroach[2] |
| 1,2-dibromoethane | 97 | 100 |
| 1-iodopropane | 100 | 100 |
| iodoethane | 100 | 100 |
| iodomethane | 100 | 100 |
| diiodomethane | 40 | 39 |
| 1,3-diiodopropane | 0 | 0 |
| 1,4-diiodobutane | 0 | 0 |
| 1,8-diiodooctane | 0 | 0 |
| 1,6-diodohexane | 0 | 5 |
| 1,5-diiodopentane | 0 | 11 |
| iodoform | 0 | 1 |
| 1,2-diiodoethane | 40 | 8 |
| tetraiodoethylene | 0 | 0 |
| Untreated control | 0 | 0 |

[1]*Blattella germanica* (L.); 30–60 adult males.
[2]*Periplaneta americana* (L.); 8–36 adult males.

Shown in Table 2 is the toxicity of both monoiodinated and diiodinated hydrocarbons to the German and American cockroach and the Cowpea weevil after 24 hours of exposure. It can be seen from Table 2 that along with the monoiodinated hydrocarbons, some of the diiodinated were just as effective at killing the tested insects over a 24-hour period. It is believed that over a longer period of time the less volatile diiodinated hydrocarbons build up a significant concentration within the insect to be lethal. The volatile monoiodinated hydrocarbons more easily saturate the air with a greater concentration of a lethal dose. Thus, the insect breaths in more of the monoiodinated compound initially than the diiodinated compound.

TABLE 2

| | % Mortality after 24 h exposure | | |
|---|---|---|---|
| Compound | German cockroach[1] | American cockroach[2] | Cowpea weevil[3] |
| 1,2-dibromoethane | 100 | 100 | 100 |
| 1-iodopropane | 100 | 100 | 97 |
| iodoethane | 100 | 100 | 100 |
| iodomethane | 100 | 100 | 100 |
| diiodomethane | 100 | 100 | 100 |
| 1,3-diiodopropane | 100 | 100 | 97 |
| 1,4-diiodobutane | 70 | 33 | 47 |
| 1,8-diiodooctane | 0 | 0 | 0 |
| 1,6-diodohexane | 0 | 0 | 0 |
| 1,5-diiodopentane | 0 | 0 | 37 |
| iodoform | 83 | 100 | 100 |
| 1,2-diiodoethane | 10 | 100 | 100 |
| tetraiodoethylene | 3 | 0 | 0 |
| Untreated control | 0 | 0 | 0 |

[1]*Blattella germanica* (L.); 30–60 adult males.
[2]*Periplaneta americana* (L.); 8–36 adult males.
[3]*Callosobruchus maculatus* (F.), 30 adults.

Diiodinated hydrocarbons have generally been found to have an increased nematological activity over that of monoiodinated hydrocarbons, especially in uncovered spaces. This is due, in part, to the increased volatility of the monoiodinated compounds over the diiodinated hydrocarbons. The diiodinated hydrocarbons tend to stay reactive in the soil longer than the monoiodinated hydrocarbons.

Figure 2:
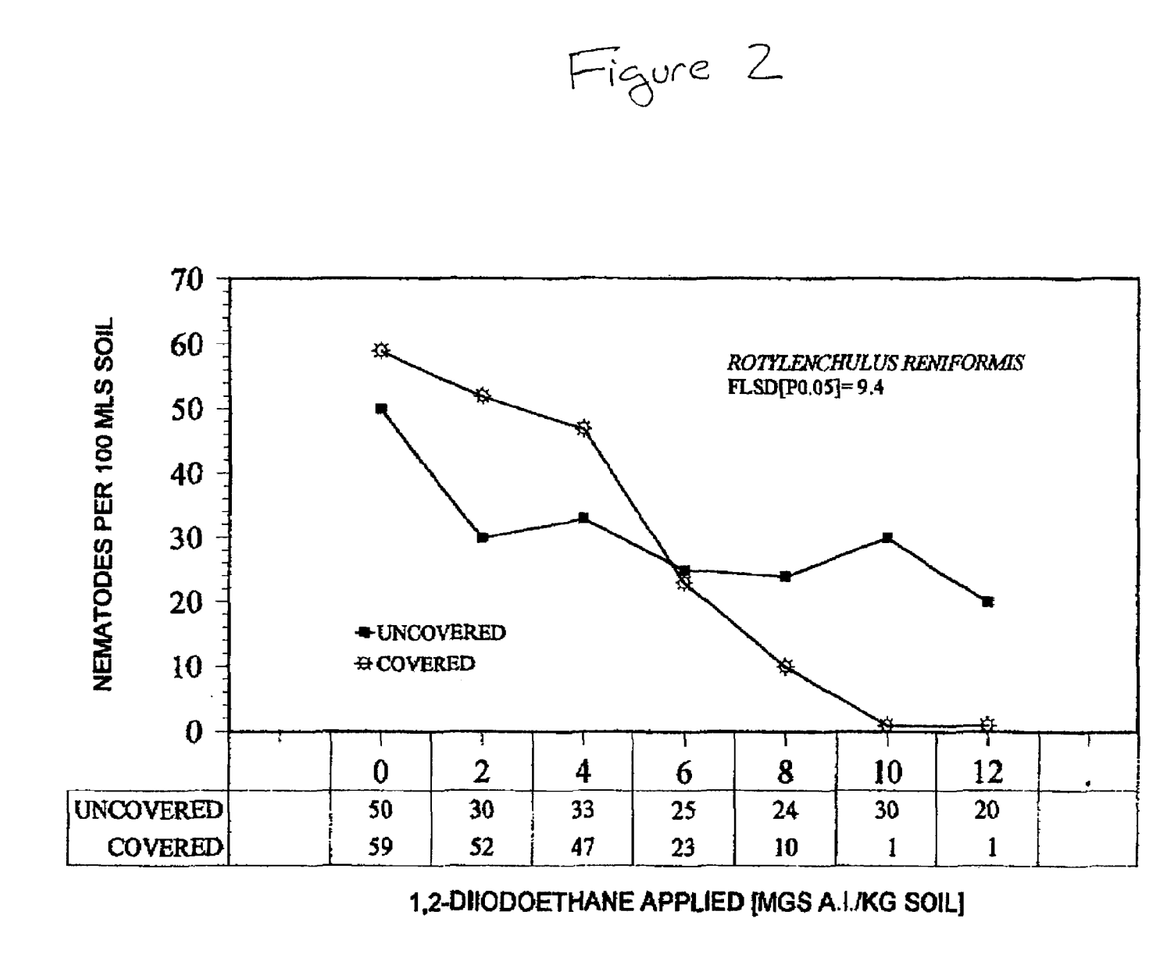
FIG. 2 depicts a graph illustrating nematicidal qualities of 1,2-diiodoethane when applied to infected soil in various dosages in an uncovered and covered state.
Figure 3:
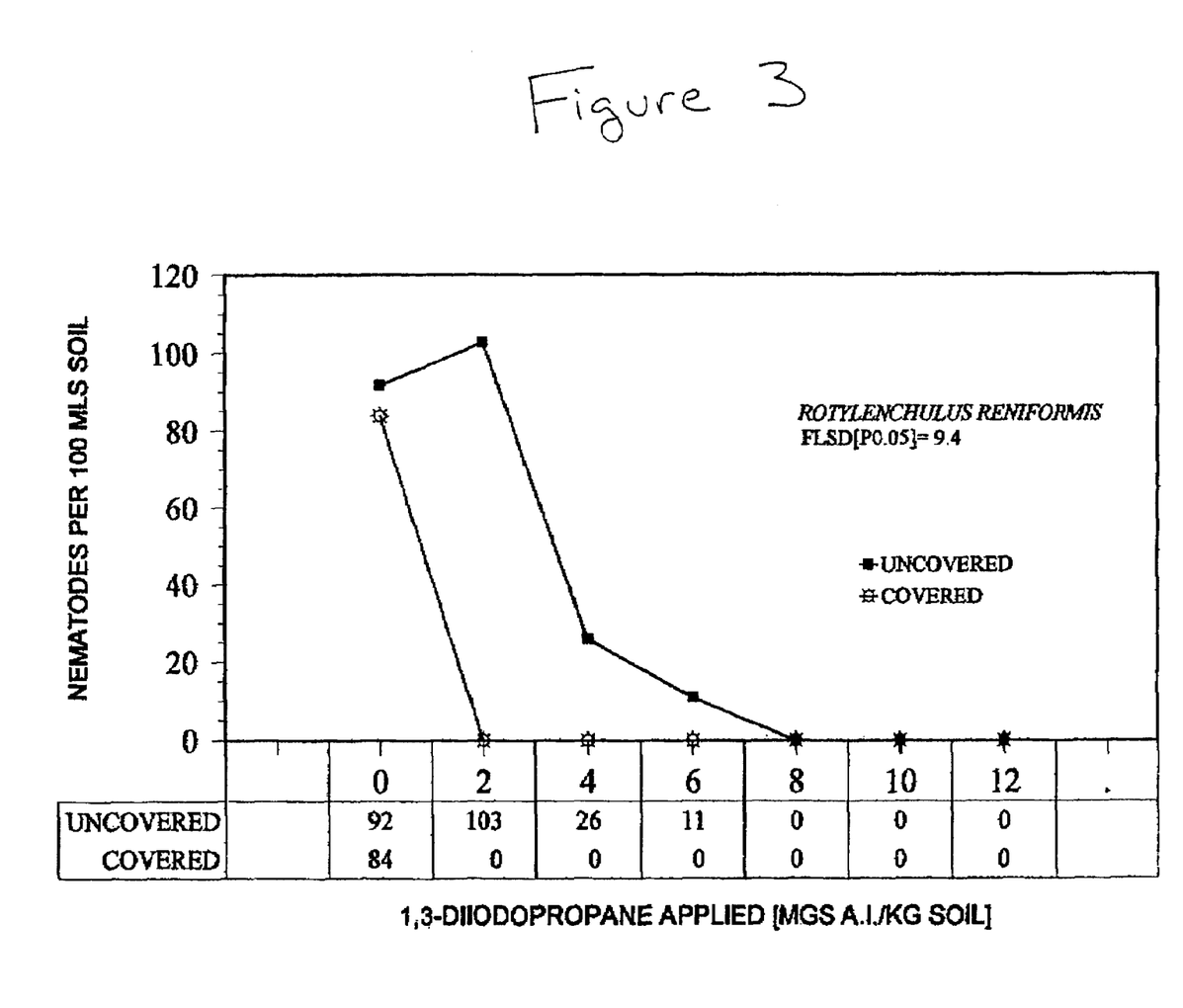
FIG. 3 depicts a graph illustrating nematicidal qualities of 1,3-diiodopropane when applied to infected soil in various dosages in an uncovered and covered state.
Figure 4:
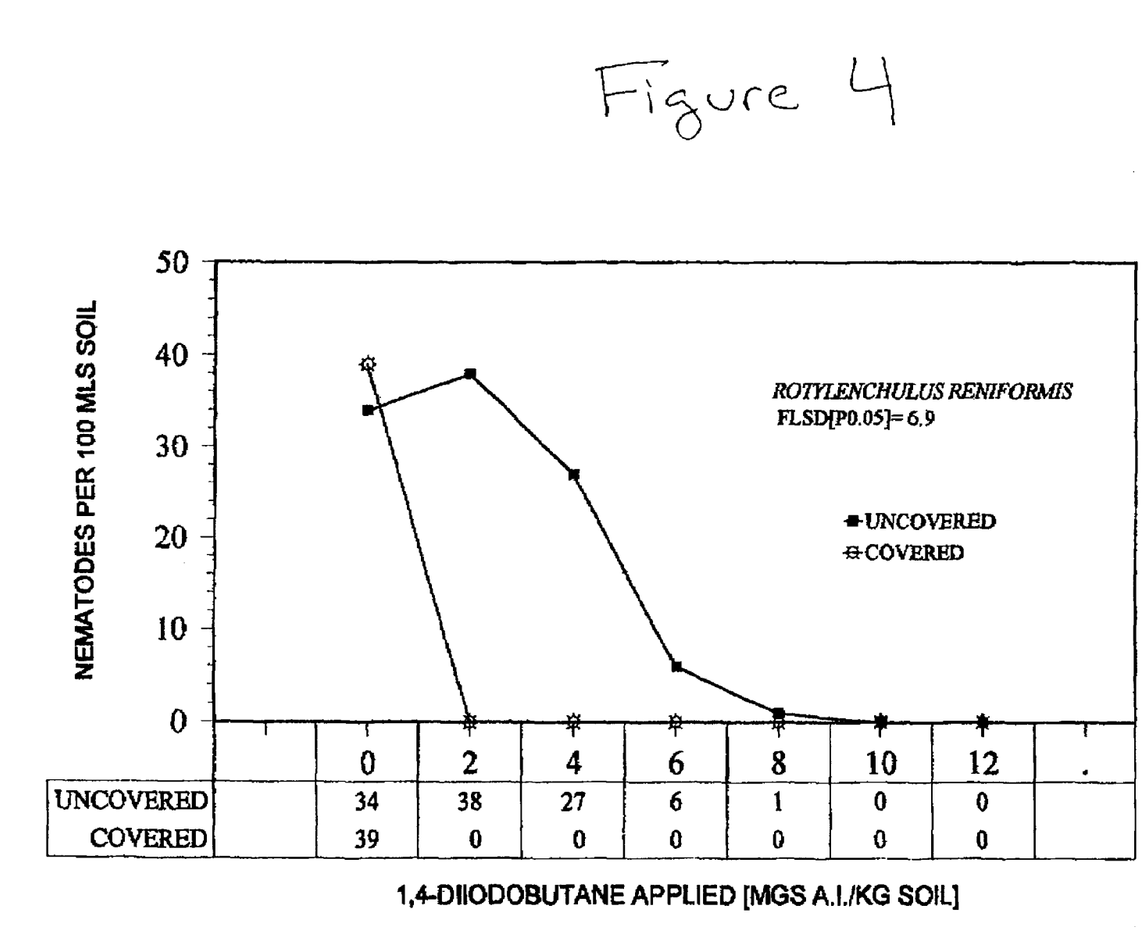
FIG. 4 depicts a graph illustrating nematicidal qualities of 1,4-diiodobutane when applied to infected soil in various dosages in an uncovered and covered state.

FIGS. 2 and 3 illustrate the effectiveness of the diiodoethane and diiodopropane in eliminating the nematode (*Rotylenchulus reniformis*) from a soil sample. The "x" axis on the top row illustrates the quantity of iodinated hydrocarbon in milligrams per kilogram of soil. The next two rows below the "x" axis indicate the number of nematodes per 100 milliliters of soil, which is also indicated on the "y" axis. In FIG. 2, 1,2-diiodoethane was applied to the soil both in a covered state and an uncovered state. As can be seen from the graph, the covered samples were more effective at eliminating the nematodes from the soil. This is believed to be so because of the volatility of 1,2 diiodoethane, wherein the cover slows down the rate at which the compound evaporates into the atmosphere. In FIG. 3, 1,3-diiodopropane was able to eliminate the nematodes from the soil in both the covered and uncovered state.

FIG. 3 illustrates that while still effective, the diiodinated hydrocarbons having more than 3 carbons, which appears to be less effective than diiodopropane. In FIG. 3, 1,4 diiodobutane is shown as having the ability to eliminate the nematodes in both the uncovered and covered state at about 10 mg per kg of soil, which is still much more effective than the standard dose of 100 mg of methyl bromide per kg of soil.

Figure 6:
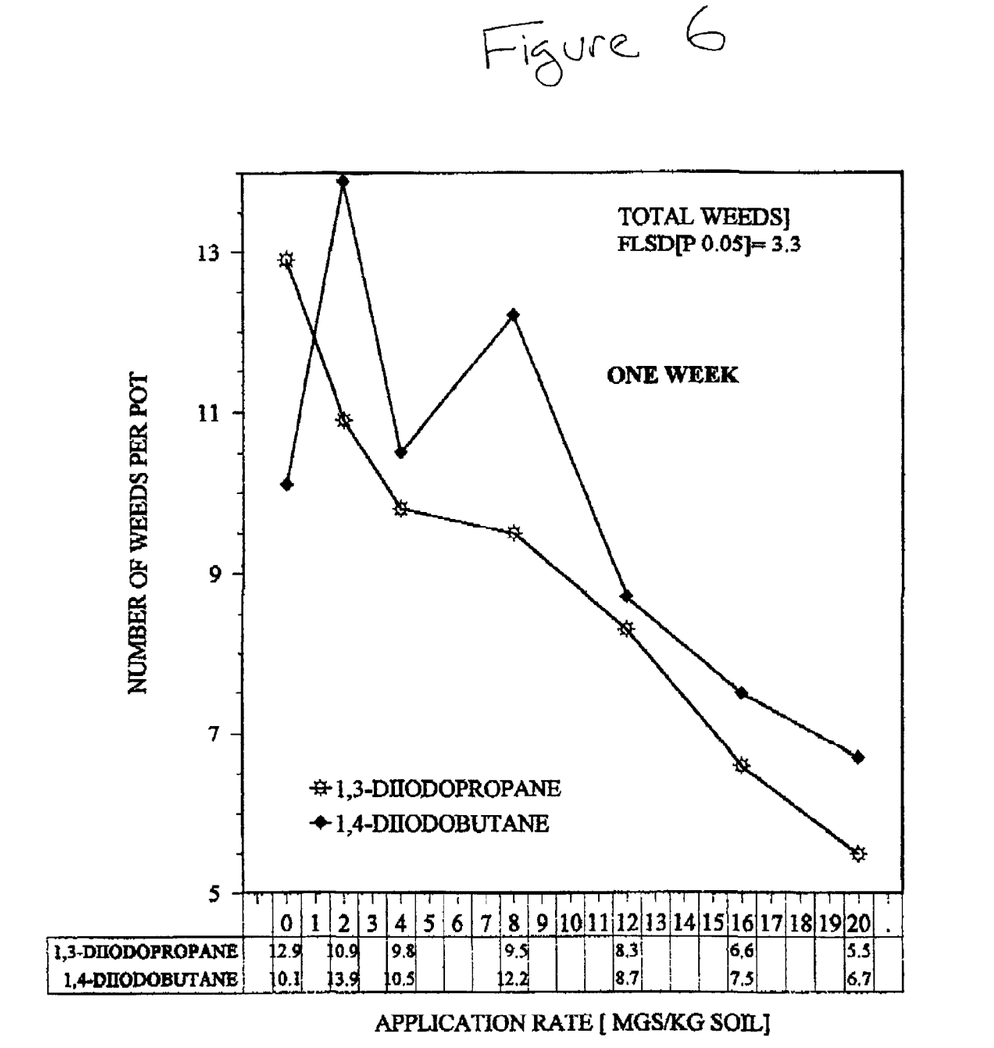
FIG. 6 depicts a graph illustrating the herbicidal qualities of 1,3-diiodopropane and 1,4-diiodobutane when applied to a potted soil containing weeds.
Figure 7:
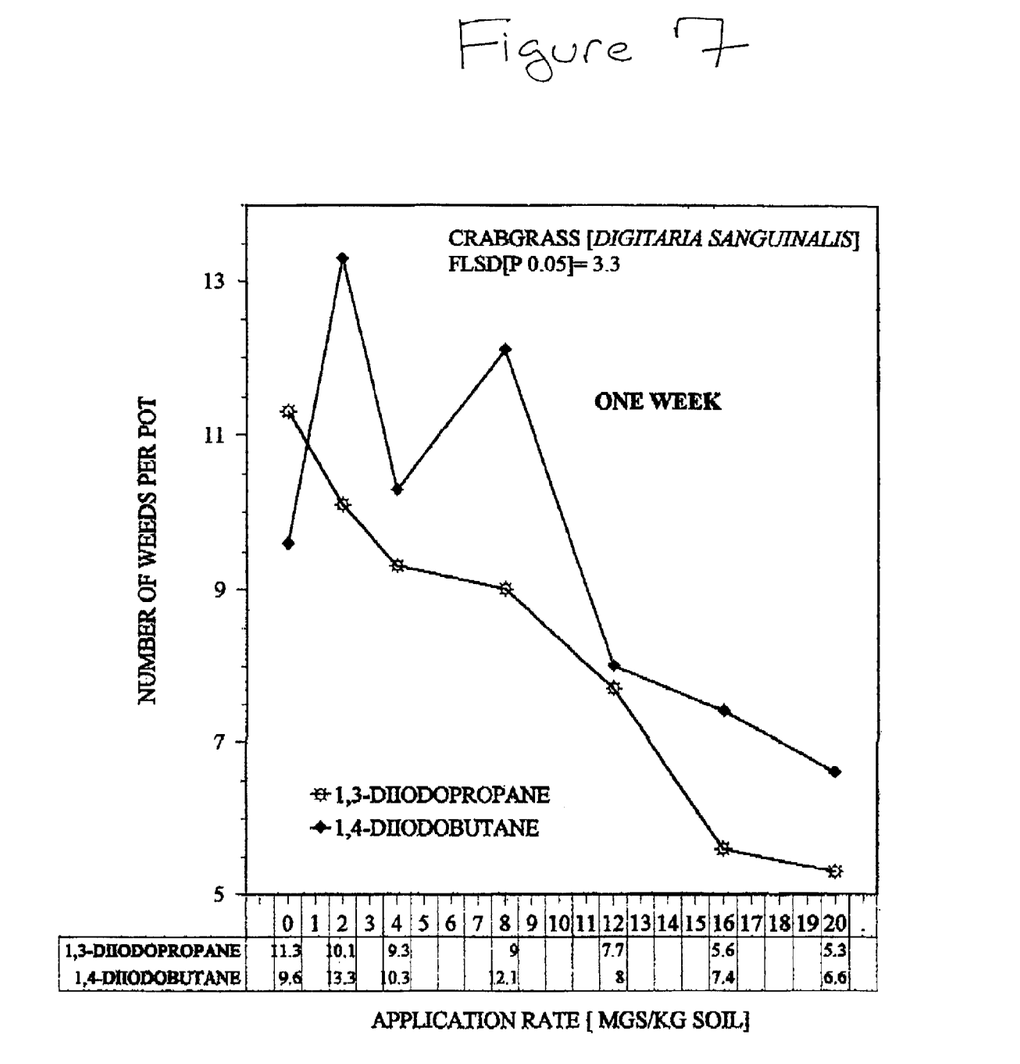
FIG. 7 depicts a graph illustrating the herbicidal qualities of 1,3-diiodopropane and 1,4-diiodobutane when applied to a potted soil containing crabgrass.

Illustrated in FIGS. 6 and 7 are the herbicidal properties of the present invention. In FIG. 6, 1,3-diiodopropane and 1,4-diiodobutane were added to a soil sample contained in a pot, wherein the number of weeds were counted at the end of a one week period. The top row of the "x" axis plots the amount in milligrams of iodinated hydrocarbon added per kilogram of soil. The two rows below the top row depict the number of weeds found after a week, which is also plotted on the "y" axis. FIG. 6 illustrates a steady decline in the number of weeds found in the pots as the dosage is increased up to 20 mg per kg of soil. 1,3-diiodopropane appears to yield better results in controlling weeds and eliminated them from the soil. It is inferred that greater dosages would eliminate an even greater number of weeds. FIG. 7 depicts similar results except that the weed controlled was only one variety: crabgrass. Again, 1,3-diiodopropane appears to yield better results in controlling and eliminating crabgrass from the soil. It is also inferred that dosages larger than 20 mg of iodinated hydrocarbons would further eliminate an even greater number of crabgrass plants.

Figure 5:
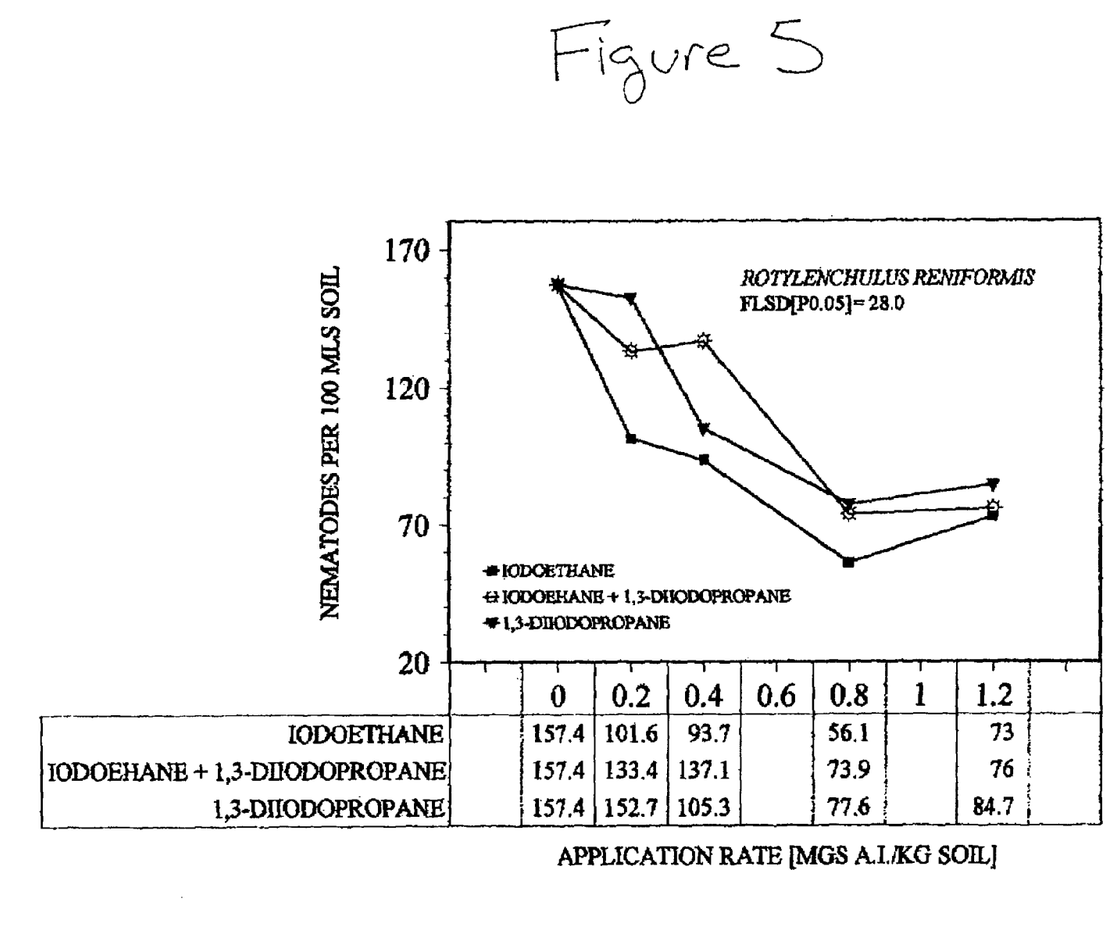
FIG. 5 depicts a graph illustrating nematicidal qualities of iodoethane, iodoethane plus 1,3-diiodopropane, and 1,3- diiodopropane when applied to infected soil in various dosages in a covered state.

FIG. 5 illustrates the combined effect of both monoiodinated and diiodinated hydrocarbons on nematodes under a covered state. The top row of the "x" axis plots the amount in milligrams of iodinated hydrocarbon added per kilogram of soil. The three rows below the top row depict the number of nematodes found for that dosage, which is also plotted on the "y" axis. Iodoethane, iodoethane +1,3 diiodopropane and 1,3 diiodopropane were tested up to a dosage of about 1.2 mg per kg of soil. FIG. 5 illustrates the effectiveness of the combined iodinated hydrocarbons in a covered state.

The ratio of monoiodinated and diiodinated hydrocarbons tested was about 1:1. This ratio was primarily chosen for convenience and is not to be thought of as limiting the present invention to any set ratio. The ratio of iodinated hydrocarbons is determined by the conditions and environment of application. Monoiodinated hydrocarbons are more volatile and thus have better penetrating characteristics than diiodinated hydrocarbons, and diiodinated hydrocarbons are less volatile which is desirable when treating soil. Thus, the ratio is determined by the desired characteristics.

While only diiodinated hydrocarbons have been illustrated in the Figures, it is fully contemplated and expected that iodinated hydrocarbons having more than 2 iodine groups, such as triiodinated hydrocarbons effective use in the present invention. The number of iodine groups has very few limitations, except those imposed by economics and the volatility of the hydrocarbon group. The same is partially true for the number carbons found in the hydrocarbon group. While it is shown that as the number of carbons increase to over 3 in the hydrocarbon, the effectiveness of the compound also decreases somewhat. But the compounds having more than 3 carbons are still effective and are fully contemplated as effective components of the present invention.

Experiment 1

In this experiment both the insecticidal and nematicidal properties of iodinated hydrocarbons were compared. In determining the insecticidal properties of the iodinated hydrocarbons, both American (*Periplaneta americana*) and German (*Blattella germanica*) cockroaches were used. Groups of cockroaches were confined in 0.95-liter glass jars with a small cotton ball. Exactly 50 μl of a test chemical was applied to the cotton ball and the jar was sealed. Knockdown, defined as the inability to walk in a coordinated manner, and mortality were assessed every 15 minutes for the first hour and hourly thereafter for 8 hours and again after 24 hours.

Monoiodo compounds [C1–C3] were found to be generally more effective than di-iodo compounds against both species. Iodomethane, iodoethane, and 1-iodopropane knocked down 100 percent of cockroaches within 1 hour after treatment and caused 100 percent mortality within 2 hours. Di-iodomethane knocked down ≈40 percent of cockroaches within 1 hour and killed 100 percent of cockroaches by 4 hours. American cockroaches were more sensitive to 1,6-diiodohexane and 1,5-diiodopentane and iodoform than German cockroaches. Diiodomethane and 1,4-diiodobutane were repellent to German cockroaches. Several diiodinated compounds did not cause mortality even after 24 hours of continuous exposure.

Additionally, the nematicidal properties of iodinated hydrocarbons were investigated in greenhouse experiments with field soil infested with *Meloidogyne arenaria* and *Heterodera Glycines*. Chemicals were added directly to infested solid at rates <100 mg/Kg soil. Treated soil was kept moist (approximately 60 percent field capacity) and uncovered for 7–10 days when samples were collected, and the pots were planted with 'Brim' soybean, *Glycine max*. Diiodo compounds were generally more effective in controlling nematodes and reducing root gall formation by *M arenaria* than the monoiodo hydrocarbons; however, there were significant differences in nematicidal properties among the diiodo compounds. 1,2-diiodoethane (C2), 1,3-diiodopropane (C3), 1,4-diiodobutane (C4), 1,5-diiodopentane (C5), 1,6-diiodohexane (C6), and 1,8-diiodobutane were applied to soil rates of 2.5, 5.0, 7.5, and 10 mg/Kg soil. All rates of C2 and C8 were ineffective in reducing *M. arenaria* juvenile (J2) populations in preplant samples. This was also true for C2 and J2 populations of *H. glycines*; however, C2 rates ≧5.0 mg suppressed J2 populations of *H. glycines*. C3, C4, C5, and C6 applied at rates of ≧5.0 mg virtually eliminated J2 populations of *M. arenaria* and *H. glycines* in preplant samples. *H. glycines* J2 numbers in final soil samples were generally inversely related to rates for C3–C8. This pattern of suppression in J2 numbers was also applicable to *M arenaria* in the final soil samples, but only for C3–C6, C2 applications resulting in either no change in *H. glycines* J2 numbers or in increased numbers. Final numbers of *M. arenaria* J2's in soil increased directly with C2 dosage but did not change significantly in response to C8 rates. Applications of C3–C6 to soil increased shoot weights in a manner directly related to dosages but only in a curvilinear pattern. Number of galls/g root and root-knot index values declined proportionately to increasing rates of C3–C6, but the opposite was observed for C2 and C8. Results showed that C3–C6 were the most nematicidal of the iodinated hydrocarbons tested.

The toxicity of iodinated hydrocarbons differs somewhat between insects and nematodes, indicating possible modes of different actions of iodinated hydrocarbon compounds between phyla. Because of their chemical properties, most notably their solubility, low molecular weight mono- and diiodinated hydrocarbons can be combined to make an effective insecticidal and nematicidal formulation that performs as well as methyl bromide against insects and nematodes.

Experiment 2

In this experiment, the nematicidal properties of various diiodinated hydrocarbons were compared. The nematicidal properties of diiodinated C2–C8 normal hydrocarbons was assessed in a greenhouse experiment with field soil infested with *Meloidogyne arenaria* [Ma] and *Heterodera glycines* [Hg]. 1,2-diiodoethane [C2], 1,3-diiodopropane [C3], 1,4-diiodobutane [C4], 1.5-diiodopentane [C5], 1,6-diiodohexane [C6] and 1,8-diiodooctane [C8] were applied to soil at rates of 2.5, 5.0, 7.5, and 10.0 mgs/kg soil. The potted soil was kept moist in a greenhouse for 10 days when preplant samples were collected for analysis, and the pots were planted with 'Brim' soybean [*Glycine max*]. After 7 weeks of growth, the plants were removed and final soil samples taken. Data was collected on weights of fresh roots and shoots, root galling by Ma, and numbers of nematodes in soil and roots. All rates of C2 and C8 were ineffective in reducing Ma juvenile [J2] populations in the preplant samples. This was also true for C2 and J2 populations of Hg; however, C8 rates $\geq 5.0$ mg suppressed J2 populations of Hg. C3, C4, C5 and C6 applied at $\geq 5.0$ mg virtually eliminated J2 populations of Ma and Hg in preplant samples. Hg J2 numbers in final soil samples were generally inversely related to rates for C3–C8. This pattern of suppression in J2 numbers was also applicable to Ma in the final soil samples but only for C3–C6. C2 applications resulted in either no change in Hg J2 numbers or in increased numbers. Final numbers of Ma J2's in soil increased directly with C2 dosage but did not change significantly in response to C8 rates. Applications of C3–C6 to soil increased shoot weights in a manner directly related to dosages but non-linear in pattern. C2 and C8 increased shoot weights slightly with the 2.5 mg rate but had no significant effect on the variable at higher rates. Number of galls/gm root and root-knot index values declined proportionately to increasing rates of C3–C6, but the opposite was observed for C2 and C8. Results showed that C3–C6 were the most nematicidal among the compounds tested.

Experiment 3

In this experiment, the nematicidal activities of iodinated hydrocarbons were compared. The effect of progressive iodination of methane on the nematicidal properties of resulting iodo-compounds was studied in a greenhouse experiment with field soil infested with root-knot [*Meloidogyne arenaria*] and soybean cyst [*Heterodera glycines*] nematodes. Methyl iodide, diiodomethane, tri-iodomethane and tetraiodomethane were applied to soil at rates of 10, 20, 40, 60, and 80 mgs/kg soil.

Following treatment, the soil was potted and maintained moist in a greenhouse for 12 days when preplant samples were taken for nematological analysis and pots were planted with 'Brim' soybean. The plants were allowed to develop for 6 weeks when they were removed from soil to determine the weights of fresh shoots and roots, root galling by *M. arenaria*, and root and soil samples were incubated to assess nematode populations. Preplant samples showed that all compounds reduced numbers of *M arenaria juveniles*[J2] in soil when applied at >10 mg/kg soil. This same pattern of nematicidal activities was also observed for *H. glycines* except that the compounds were generally more effective against root-knot nematode. The compounds had no significant effect on shoot weights when applied at rates $\leq 40$ mg/kg of soil; however, the 60 and 80 mg rates of tri- and tetra-iodomethane reduced shoot weights. Data on number of root galls, root-knot index values and soil and root J2 populations of *M arenaria* and *H. glycines* at the end of the experiment indicated that the overall order of nematicidal activity among the compounds was tetra-iodomethane$\geq$tri-iodomethane>di-iodomethane>methyl iodide. Overall order of activity against *M arenaria* was tetra-iodomethane>tri-iodomethane>di-iodomethane>methyl iodide Experiment 4

In this experiment, the nematicidal properties of low molecular weight iodinated hydrocarbons were investigated. The nematicidal properties of iodinated C1–C3 hydrocarbons were evaluated in greenhouse experiments with field soil infested with root-knot [*Meloidogyne arenaria*] and cyst [*Heterodera glycines*] nematodes. Iodomethane, di-iodomethane, iodoethane, di-iodoethane, and 1-iodopropane were added to soil at rates of 0.1, 0.2 and 0.4 ml/kg soil.

The treated soil was kept moist for 10 days when soil samples were taken for nematode analysis and 'Brim' soybean [*Glycine max*] planted. Soybeans were allowed to grow for 8 weeks and then were removed from the soil to determine plant growth, root-knot indices and the number of galls generated by *M arenaria*. All rates of the di-iodo compounds resulted in elimination of *M. arenaria* [J2] juvenile populations in soil 10 days after application of the compounds; *H. glycines* J2 populations were eliminated by all dosages of diiodomethane but only by the 0.4 ml rate of diiodoethane. Iodoethane and 1 iodopropane were ineffective for control of *M. arenaria* and *H. glycines*. *M. arenaria* J2 soil populations increased directly in response to rates of iodopropane. Iodomethane eliminated root-knot nematode juveniles and reduced *H. glycines* J2 populations when applied at the 0.4 ml rate but was ineffective at lower rates. Diiodo compounds were the most effective of all compounds in suppressing root galling by *M. arenaria*. Significant suppression of gall formation was obtained with iodomethane and iodoethane applied at $\geq 0.2$ ml/kg soil; 1 iodopropane had no significant effect on root knot. All compounds except 1-iodopropane increased fresh shoot weight when applied at $\geq 0.1$ ml/kg soil. Results indicate that the diiodo hydrocarbons are more effective nematicides than the mono-iodo compounds.

Experiment 5

In this experiment, the nematotoxic properties of ethylene diiodide were compared to that of methyl iodide. The nematicidal efficacies of iodomethane [IM] and ethylene diiodide [EDI] were compared in a greenhouse experiment using field soil infested with *Meloidogyne arenaria, Pratylenchus brachyurus*, and *Paratrichodorus christiei*.

Each compound was added to soil at rates of 100, 200, 300 and 400 mg s/kg of soil. The soil was potted and kept moist for two weeks when it was planted with 'Brim' soybean after taking samples for nematological analyses. After eight weeks of growth, the plants were removed from the pots and soil samples taken. Data was collected on weights of fresh roots and shoots, general appearance of roots [root condition index] and root gall formation by *M. arenaria*. All EDI rates eliminated *M. arenaria* juveniles [J2] and populations of the other nematodes in the preplant samples; IM reduced J2 numbers by 50–70%, eliminated *P. christiei* with the 400 mg rate, but had no effect on *P. brachyurus*. There were no galls in roots of plants from EDI-treated soil, but significant numbers in those from soils treated with MI. A general increase in weights of shoots and roots was observed in response to the two lowest rates of the two compounds; however, EDI at 400 mg was phytotoxic. The general appearance of roots was improved by EDI at rates $\leq 300$ mg, but MI had no effect on the variable. EDI applications resulted in roots and soils with no nematodes. *M. arenaria* J2 populations in roots were reduced by 60–70% by MI treatments, but the compound had no effect on root populations of *P. brachyurus*. MI had no effect on J2 populations in the final soil samples, although it suppressed *P. christiei*, by 50–70%. Results indicate that EDI is a better nematicide than MI.

Experiment 6

In this experiment, the pesticidal and herbicidal properties of volatile, low molecular weight, iodinated hydrocarbons were investigated. The relative nematicidal efficacy of iodomethane [C1], 1,2-diiodoethane [C2], 1,3-diiodopropane [C3] and 1,4-diiodobutane [C4] was studied in greenhouse experiments with soil from a cotton field infested with the reniform nematode [Rotylenchulus reniformis]. The chemicals were obtained from Aldrich, Milwaukee, U.S.A. Emulsifiable concentrates of the compounds were prepared by dilution in acetone containing an emulsogen.

For each chemical, an aqueous emulsion with 0.2% [w/w] of the compound was prepared and was applied to soil at rates of 2, 4, 6, 8, 10, and 12 mgs a.i./Kg soil. The treated soil was mixed and transferred to 1L capacity 10-cm diameter cylindrical pots. Pots with untreated soil [control] and with treated soil were placed on a greenhouse bench in a randomized complete block design. Each treatment was represented by 14 replications [pots], one half of which were left uncovered, and the other 7 were covered with polyethylene plastic bags [approx. 1 mil thickness] retained with a rubber around the pots. Soil samples for nematological analysis [salad bowl incubation technique] were collected 7–10 days after application of the materials. All rates of C1 failed to control the nematode in the covered and the uncovered pots. Numbers of the nematode in soil declined linearly in response to C2 rates. In covered pots, applications of the material were particularly effective resulting in 100% kill with the 10 and 12 mg rates. All dosages of C3 and C4 eliminated the nematode in covered pots. In uncovered pots, C3 was somewhat more effective than C4 at rates $\leq 6$ mgs/Kg soil, but applications of both compounds at the 3 highest rates resulted in 100% mortality. In a greenhouse experiment of similar design to the nematicide experiments, the C3 and C4 emulsions were applied at rates of 2–20 mgs a.i./Kg soil to a soil infested with crabgrass [*Digitaria sanguinalis*], purple nutsedge [*Cyperus rotundus*], Jimson weed [*Datura stramonium*] and a variety of other weed species. All pots were covered, and the number of weeds were counted 7, 14 and 30 days after application of the chemicals. Results indicated that C3 was significantly more effective in controlling weeds than C4 and that rates $\geq 16$ mgs/Kg soil were necessary to have satisfactory weed control.

While specification embodiments have been set forth as illustrated and described above, it is recognized that variations may be made with respect to disclosed embodiments. Therefore, while the invention has been disclosed in various forms only, it will be obvious to those skilled in the art that many additions, deletions and modifications can be made without departing from the spirit and scope of this invention, and no undue limits should be imposed except as set forth in the following claims.

What is claimed is:

1. A method of controlling deleterious organisms comprising: applying to soil or atomosphere an effective amount of a compound comprising mono-iodinated hydrocarbons and diiodinated hydrocarbons to control said organisms.

2. The method of claim 1, wherein the hydrocarbon group is selected from a carbon chain having between about 1 to 6 carbons.

3. The method of claim 1, wherein the diiodinated hydrocarbons are selected from the group consisting of diiodomethane, diiodoethane, diiodopropane and combinations thereof.

4. The method of claim 1, wherein the diiodinated hydrocarbons are selected from the group consisting of diiodobutane, diiodopentane, diiodohexane and combinations thereof.

5. The method of claim 1, wherein the mono-iodinated hydrocarbons are selected from the group consisting of iodomethane, iodoethane, iodopropane, and combinations thereof.

6. The method of claim 1, wherein the compound comprises iodoethane and 1,3 diiodopropane.

7. The method of claim 1, wherein the compound comprises mono-iodinated hydrocarbons and diiodinated hydrocarbons in a ratio of about 1:1.

8. The method of claim 1, wherein the compound is applied as a fumigant.

9. The method of claim 8, wherein the effective amount is at least about 0.1 mg of compound per liter of air.

10. The method of claim 9, wherein the effective amount is at least about 2 mg of compound per liter of air.

11. The method of claim 1, wherein the effective amount is at least about 2 mg per kg of soil.

12. The method of claim 11, wherein the effective amount is between about 2 mg to 12 mg per kg of soil.

13. The method of claim 1, wherein the compound is a herbicide and having an effective amount of at least 20 mg per kg of soil.

14. A method of soil fumigation comprising:
applying to the soil an effective amount of a fumigant selected from the group consisting of diiodinated hydrocarbons, polyiodinated hydrocarbons and combinations thereof.

15. The method of claim 14, wherein the hydrocarbon comprises a carbon chain having between about 3 to 6 carbons.

16. The method of claim 14, wherein the effective amount is between about 2 to 10 mg of compound per kg of soil.

17. The method claim 14, wherein the iodinated hydrocarbon is selected from the group consisting of tetra-iodomethane, tri-iodomethane, diiodomethane and combinations thereof.

18. The method of claim 14, wherein the iodinated hydrocarbon comprises an ethylene diiodide.

19. The method of claim 18, wherein the effective amount of fumigant added to the soil is at least about 300 mg of ethylene diiodide per kg of soil.

20. The method of claim 1, wherein the compound is a herbicide.

21. A pesticide for controlling deleterious organisms comprising:
a composition comprising mono-iodinated hydrocarbons and di-iodinated hydrocarbons, wherein the di-iodinated hydrocarbons are selected from the group consisting of di-iodomethane, di-iodoethane, di-iodopropane, diiodobutane, diiodopentane, diiodohexane and combinations thereof.

22. A pesticide for controlling deleterious organisms comprising:
a composition comprising mono-iodinated hydrocarbons and di-iodinated hydrocarbons, wherein the mono-iodinated hydrocarbons are selected from the group consisting of iodomethane, iodoethane, iodopropane, and combinations thereof.

23. The pesticide of claim 22, wherein the composition comprises iodoethane and 1,3 di-iodopropane.

24. The pesticide of claim 22, wherein the ratio of the mono-iodinated hydrocarbons and the di-iodinated hydrocarbons is about 1:1.

25. A pesticide for controlling deleterious organisms comprising:
a compound selected from the group consisting of di-iodinated hydrocarbons, polyiodinated hydrocarbons and combinations thereof and optionally a pesticide; and
wherein the hydrocarbon comprises a carbon chain having between about 3 to 6 carbons.

26. The pesticide of claim 25, wherein the pesticide is added in an effective amount between about 2 mg to 10 mg of compound per kg of soil.

* * * * *